(12) United States Patent
Classens

(10) Patent No.: US 7,097,057 B2
(45) Date of Patent: Aug. 29, 2006

(54) CLOSURE DEVICE FOR A VACUUM SAMPLE COLLECTOR

(75) Inventor: Albert Louis Classens, Houthalen (BE)

(73) Assignee: Helvoet Pharma Belgium N.V., (BE)

( * ) Notice: Subject to any disclaimer, the term of this patent is extended or adjusted under 35 U.S.C. 154(b) by 175 days.

(21) Appl. No.: 10/168,635

(22) PCT Filed: Dec. 22, 2000

(86) PCT No.: PCT/EP00/13169

§ 371 (c)(1),
(2), (4) Date: Nov. 4, 2002

(87) PCT Pub. No.: WO01/47636

PCT Pub. Date: Jul. 5, 2001

(65) Prior Publication Data

US 2004/0118803 A1    Jun. 24, 2004

(30) Foreign Application Priority Data

Dec. 23, 1999 (DE) .............................. 199 62 664

(51) Int. Cl.
*B65D 41/20* (2006.01)
(52) U.S. Cl. .............. 215/247; 215/DIG. 3; 220/254.1; 604/415
(58) Field of Classification Search ................ 215/247, 215/DIG. 3, 249, 251; 220/254.1; 604/415
See application file for complete search history.

(56) References Cited

U.S. PATENT DOCUMENTS

| | | | | |
|---|---|---|---|---|
| 4,967,919 A | * | 11/1990 | Earhart | 215/247 |
| 5,232,111 A | | 8/1993 | Burns | |
| 5,275,299 A | * | 1/1994 | Konrad et al. | 215/341 |
| 5,360,012 A | | 11/1994 | Ebara et al. | |
| 5,361,921 A | * | 11/1994 | Burns | 215/320 |

(Continued)

FOREIGN PATENT DOCUMENTS

EP    0 029 126 A1    10/1980

(Continued)

*Primary Examiner*—Nathan J. Newhouse
*Assistant Examiner*—James Smalley
(74) *Attorney, Agent, or Firm*—Eugene E. Renz, Jr.

(57) ABSTRACT

The invention relates to a closure device for a vacuum sample collector, comprising an external cap (2), in a hard material, preferably a hard plastic component, with a top face (4) and a side skirt (5) surrounding the above, which may be connected to a sleeve-like opening section of the vacuum sample collector, and a sealing element (3) arranged on the container side of the external cap (2) made from an elastic material, preferably a soft synthetic component. The external cap (2) is turned inwards on its top face (4), and the section of the cap turned inwards forms a depression, the floor of which (10) has a turned-up section which faces outwards and which forms an essentially cylindrical projection (11), with a flat opening (12) and which, within the depression, terminates in an opening (13), arranged in a recessed manner with relation to the front face of the external cap (2), such that said opening is outside the contact area of a finger. The sealing, element (3) fills the opening (12) and, furthermore, lines the inner wall of the inverted section (8) and a groove (19), which is formed on the inner side of a front face of the external cap (2) between the side skirt (5) and the inverted section (8), whereby a gap (22) remains on the inner wall (21) of the side skirt (5) to accept the sleeve-like opening section of the vacuum sample collector in a sealed manner. The invention further relates to a vacuum sample collector.

3 Claims, 5 Drawing Sheets

U.S. PATENT DOCUMENTS

Figure 1:
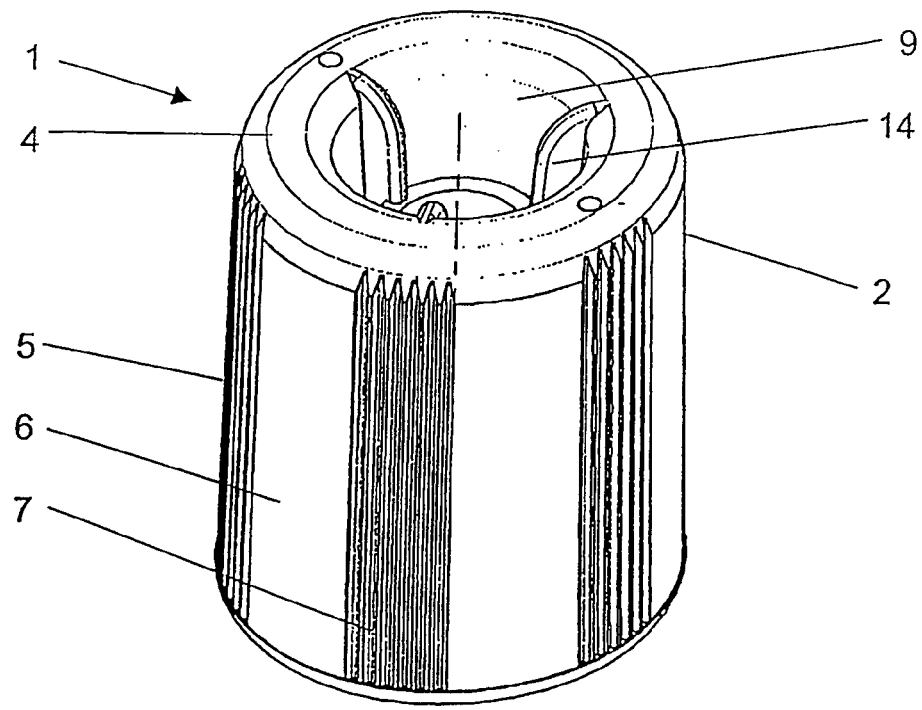

| | | | |
|---|---|---|---|
| 5,494,170 A * | 2/1996 | Burns | 215/247 |
| 5,522,518 A * | 6/1996 | Konrad et al. | 215/247 |
| 5,632,396 A * | 5/1997 | Burns | 215/247 |
| 5,699,923 A | 12/1997 | Burns | |
| 5,738,233 A * | 4/1998 | Burns | 215/247 |
| 5,779,074 A * | 7/1998 | Burns | 215/247 |
| 6,006,931 A * | 12/1999 | Sarstedt | 215/247 |
| 6,426,049 B1 * | 7/2002 | Rosen et al. | 422/102 |
| 6,510,969 B1 * | 1/2003 | Di Giovanni et al. | 222/402.2 |
| 6,562,300 B1 * | 5/2003 | Rosen et al. | 422/102 |

FOREIGN PATENT DOCUMENTS

| | | | |
|---|---|---|---|
| EP | WO 81/01238 | 5/1981 | |
| EP | 0 022 765 B1 | 10/1983 | |
| EP | 0 129 029 A1 | 12/1984 | |
| EP | 0 150 172 | 11/1985 | |
| EP | 0 189 391 A2 | 1/1986 | |
| EP | WO 89/09735 | 10/1989 | |
| EP | 0 454 493 A2 | 10/1991 | |
| EP | WO 95/17253 | 6/1995 | |
| EP | 0 445 707 B1 | 8/1995 | |
| EP | 0 623 523 B1 | 6/1997 | |
| EP | 1 064 879 A1 | 1/2001 | |

* cited by examiner

CLOSURE DEVICE FOR A VACUUM SAMPLE COLLECTOR

The invention relates to a closure device for a vacuum sample collector.

Such closure devices are used mainly for blood sample tubes when taking blood samples. The blood sample tubes, initially empty, containing a vacuum and sealed with a closure device, are punctured in the region of the closure device, when taking a blood sample, by a first end of a double-ended cannula, whose second end is inserted into a vein of a person. The vacuum prevailing in said blood sample tube causes blood to be drawn into the blood sample tube. Once the tube is full, it is pulled off the cannula together with the closure device, said closure device causing automatic sealing of the blood sample tube. A further blood sample tube having a closure device may be connected to the cannula, which may still be attached to the person, in order to draw a further quantity of blood.

In a laboratory, the closure device is removed from the blood sample tube, so that the blood may be analyzed. A different possibility consists in puncturing the closure cap and drawing a sample by means of a cannula.

The closure device may also be used for other purposes which require sealing of a sample collector with a lower internal pressure relative to the environment. The internal pressure within the sample collector is made to effect suction of a liquid, during the process of taking a sample, by suspending the sealing of the sample collector against the environment in the region of the closure device using a hollow needle.

All applications require that the closure device tightly seal the vacuum sample collector in order to maintain the vacuum until the time of use and to avoid contamination of the contents of the collector with contaminants which would distort the analytic result.

Furthermore, the puncturing of the closure device using a cannula is to be effected with as little resistance as possible. This is particularly desirable if the closure device is used in connection with a blood sample tube, since, in taking blood samples, in most cases, several tubes are filled, while the cannula remains inserted in the person. Stronger resistance to puncturing of the closure device may be painfully felt by the person.

However, despite a weak puncturing force, the cannula is to be securely held in the closure device when a blood sample is taken. Therefore, the reduction of the resistance to puncturing is opposed by the additional requirement of sufficient fixing of the cannula during the process of taking a sample.

When taking a blood sample, a drop of blood will sometimes remain on the tip of the cannula during removal of the blood sample tube from the cannula, which drop spreads at the puncture in the closure device. If the puncture is within reach of the fingers of a person handling the blood sample tube, there is an increased risk of infection for said person. In addition, removal of the cannula from the closure device may produce splashing effects. These occur, for example, when the material exhibits a poor shape memory around the puncture and does not close again fast enough upon withdrawing the cannula from the closure device. Also, when opening the closure device at the laboratory, it is to be ensured that, when removing the residual vacuum still remaining in the blood sample tube, no splashing effects are produced on the outside.

Moreover, it is to be noted that, for reasons of sterility, the closure devices must not be used more than once, so that large numbers of said closure devices are needed. Thus, aspects pertaining to manufacturing processes and materials may be decisive for the success of the product.

The prior art discloses a multiplicity of closure devices, most of which are integrally formed from a flexible plastic or rubber material. An example of such device is given in U.S. Pat. No. 3,974,930 A. As this known closure device, in addition to a portion to be punctured, simultaneously serves to shield the vacuum, said device must be formed to have a large volume from a material having a relatively good shape memory, in order to avoid removal of the vacuum in the sample collector by inadvertently applying too much force to the closure device. The selection of the material requires great resistance to puncturing with a cannula. In order to shield the puncture against being touched by the finger of a person handling it, a narrow central conduit is provided, into which the tip of a cannula is inserted only with great difficulty and which additionally leads to a considerable wall thickness and thus a great material requirement.

Another closure device is disclosed in U.S. Pat. No. 5,494,170 A, wherein a sealing element made of an elastomer is inserted into an external cap made of hard-plastics. Said sealing element therein extends through an opening provided in the external cap and widely covers a bottom of a depression frontally provided in said external cap, so that the area to be punctured is not clearly visible from the outside. In the area to be punctured, a frustoconical elevation is provided on the sealing element to facilitate the run-off of a drop, which may sometimes be present on the tip of the cannula, into the wide area around the elevation. Both the elevation and the wide area are out of reach of a finger resting flatly against the front face of the external cap. However, the large diameter of the groove does not allow to prevent a finger tip from touching the elevation or the wide area by inappropriate handling and contacting a drop of blood there. Moreover, the use of material with respect to the more expensive soft component is not optimal. The diaphragm-like design of the external cap in the region around the puncture leads either to a great wall thickness or to unsatisfactory reinforcement of the external cap in the bottom region of the depression.

In view thereof, it is an object of the invention to provide a closure device of the above-mentioned type, which is easy to manufacture using little material while ensuring a high sealing activity, little risk of infection and little resistance to puncturing.

This object is achieved by a closure device for a vacuum sample collector, comprising an external cap made of a hard material, preferably a hard-plastic component, with a front wall and a side skirt, which surrounds said front wall and may be attached to a sleeve-like opening portion of the vacuum sample collector, and a sealing element arranged on the container side of the external cap and made of an elastic sealing material, preferably a soft-plastic component, the external cap being turned in at its front wall and the turned-in part forming a depression, at the bottom of which an outwardly directed, turned-out part is centrally provided which forms an essentially cylindrical projection comprising a smooth-surface through hole and terminating in an opening within said depression, which opening is arranged outside a contact area of a finger in a manner recessed from a front end of the external cap, wherein the sealing element fills the through hole and further lines the inside wall of the turned-in part as well as a groove, which is formed on the inner side of the front end of the external cap between the side skirt and the turned-in part, whereby a gap is formed on the inside wall of the side skirt to receive, in a sealing manner, the sleeve-like opening portion of the vacuum sample collector.

The solution according to the invention allows tight sealing of a vacuum sample collector, which is not affected even by a lateral stress applied to the external cap, because the sleeve-like opening portion is pressed against the solid inside wall of the external cap. The sealing element serves as an additional compression spring supporting the contacting force of the sleeve-like opening portion against the inside wall of the side skirt of the external cap.

The turned-out part, i.e. the essentially cylindrical projection, provided at the bottom of the depression in the external cap generates a reinforcing effect in the region of the puncture in the closure cap, which effect allows a particularly thin-walled design of the external cap in this region, while high structural strength is also achieved at the same time. In addition, the amount of the required sealing material may be reduced to a minimum. Moreover, since the sealing material is not needed to reinforce the bottom region of the depression, said material may be selected solely with a view to minimal resistance to puncturing. Thus, a closure cap is obtained which, when being used in connection with a blood sample tube, allows a blood sample to be taken in a manner causing less strain to a person, because the exchange of the tubes can be effected with little forces of reaction.

Moreover, the projection is arranged out of reach of a finger tip, so as to eliminate the risk of infection for a person handling it. In addition, by turning out the bottom region, a receiving gap is formed between the inside wall of the turned-in part and the projection to receive a drop which may possibly be present on the tip of the cannula when pulling out the latter and which is wiped off on said projection.

In an advantageous embodiment of the invention, a narrow, gap-shaped annular space is formed between the outside wall of the cylindrical projection and the inside wall of the inwardly directed, turned-in part. This prevents distribution of the drop over a large area so that its total surface area remains small. Moreover, a certain suction effect is created by the gap-shaped design, drawing the drop toward the lowest point of the annular space.

In a further advantageous embodiment, radial reinforcing ribs are preferably formed on the inside wall of the inwardly directed, turned-in part. Without an increased material requirement, said ribs reduce the free diameter of the depression such that not even a thin finger tip may enter the infectious region on said projection. This allows the depression to be formed with relatively little depth and in a manner which saves material and is safe from infection.

In a further advantageous embodiment, the radial reinforcing ribs extend into the gap-shaped annular space and divide the latter into gap-shaped pockets. This leads to a further increase in structural rigidity of the bottom region of said external cap, allowing further material savings.

It has turned out to be particularly favorable for the height of the cylindrical projection above the bottom of the turned-in part to be about half the depth of the turned-in part, because this will make sufficient receiving space available for the drop, even in the case of larger drops and a narrow gap.

In order to optimize strength, and for the above-mentioned suction effect, it is advantageous if the maximum width of the narrow, gap-shaped annular space is not more than 1.5 times the wall thickness of the turned-in part on the external cap.

In order to ensure protection against splashing, when the closure device is removed in a laboratory, said device is preferably formed such that the height of the side skirt is about twice the depth of the turned-in part.

Preferably, the use of material may be further optimized for the elastic sealing material if the sealing element extends up to an inside edge of the opening of the cylindrical projection and terminates in said opening.

For an improved run-off of a drop into the annular gap, the end of the cylindrical projection formed by the opening and by the sealing element is formed, according to a further preferred embodiment, in an outwardly bulged manner.

In a further advantageous embodiment, the closure device is provided as a bicomponent, injection-molded plastics part, achieving adhesion and, thus, high bonding strength between the external cap and the sealing element. Preferably, at least one through hole leading to the groove from the outside is provided on the front end of the external cap, in the passage from the side skirt to the turned-in part. This allows to obtain good filling behavior when injecting the sealing element during injection molding, thus keeping the number of rejects low.

In a further preferred embodiment of the invention, the external cap is made of a gas-impermeable material, preferably polypropylene, and the sealing element is made of an elastomer, preferably rubber. Such closure device exhibits much higher impermeability to gas than a cap made only of rubber.

According to the invention, a vacuum sample collector, preferably for use in taking blood samples, is further provided, said collector comprising a container having a sleeve-like opening portion which is sealed by a closure device as described above, wherein a vacuum prevails in said collector. This results in a sample collector which exhibits high sealing activity and is easily manufactured, with low risk of infection, low resistance to puncturing and little use of material.

Figure 2:
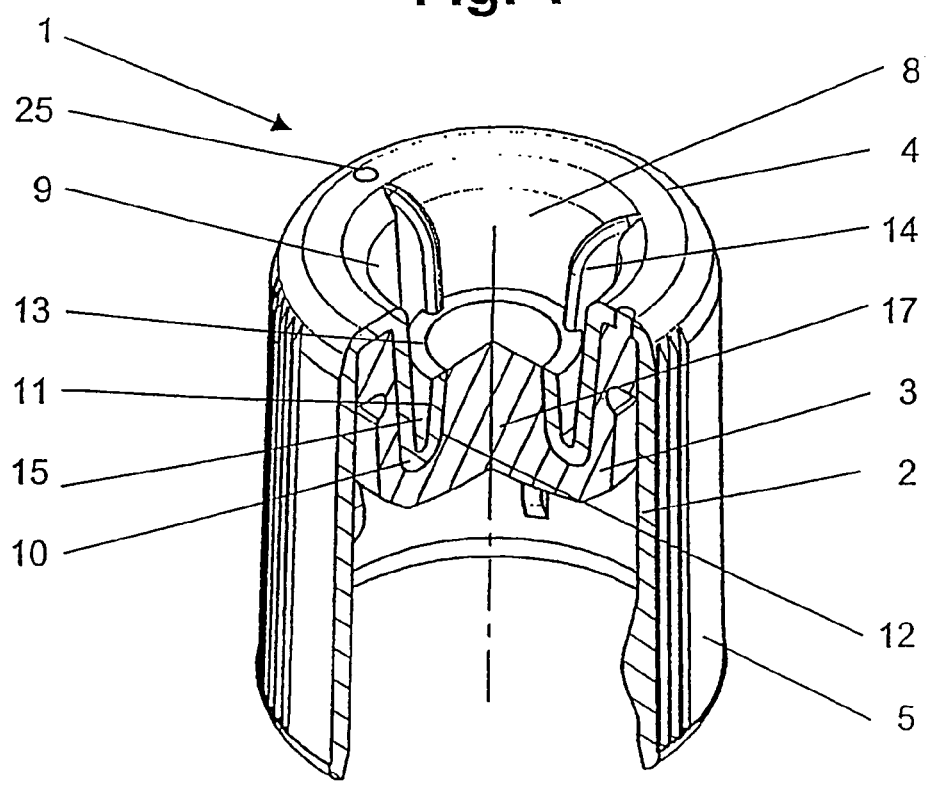
Figure 3:
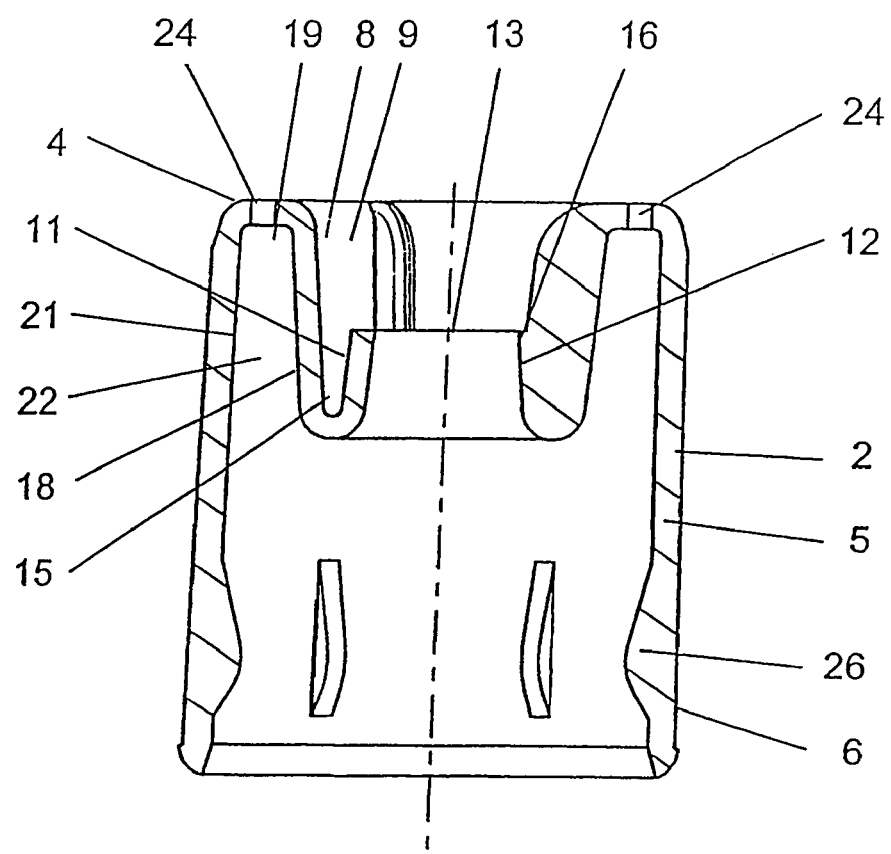
Figure 4:
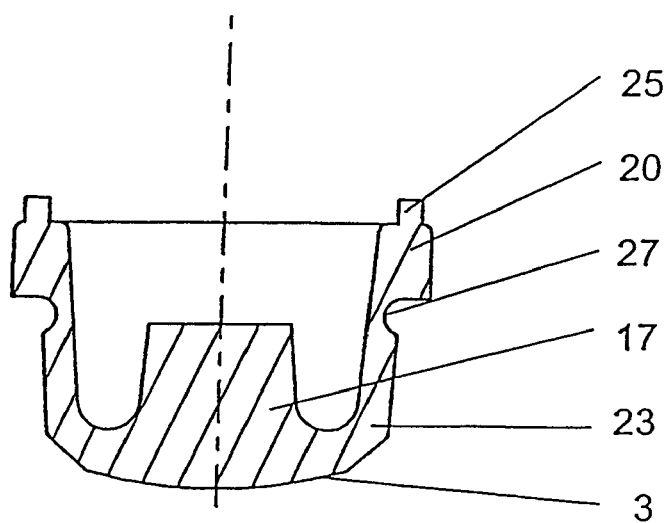
Figure 5:
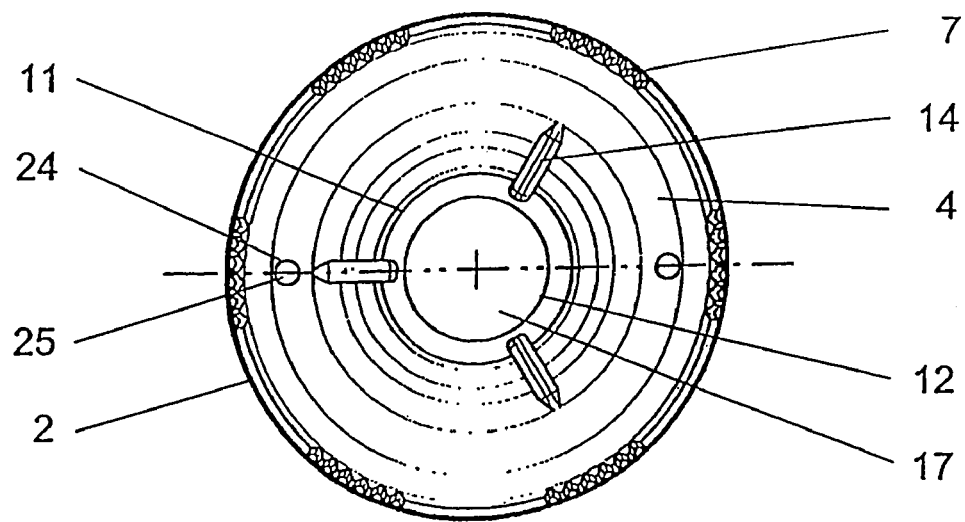
Figure 6:
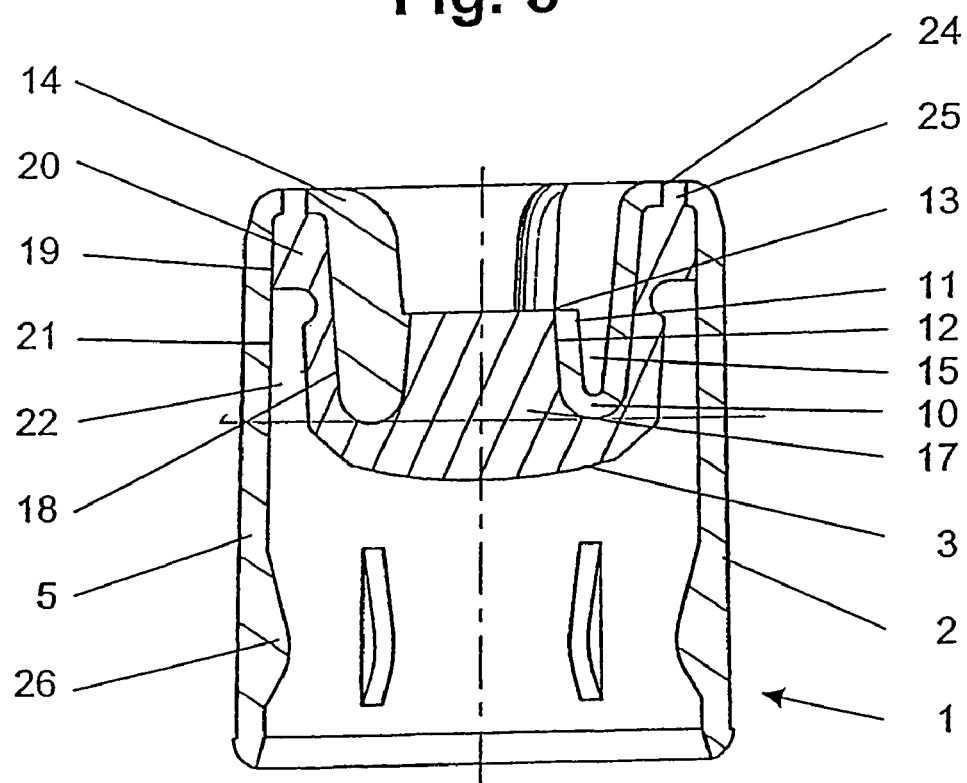
Figure 7:
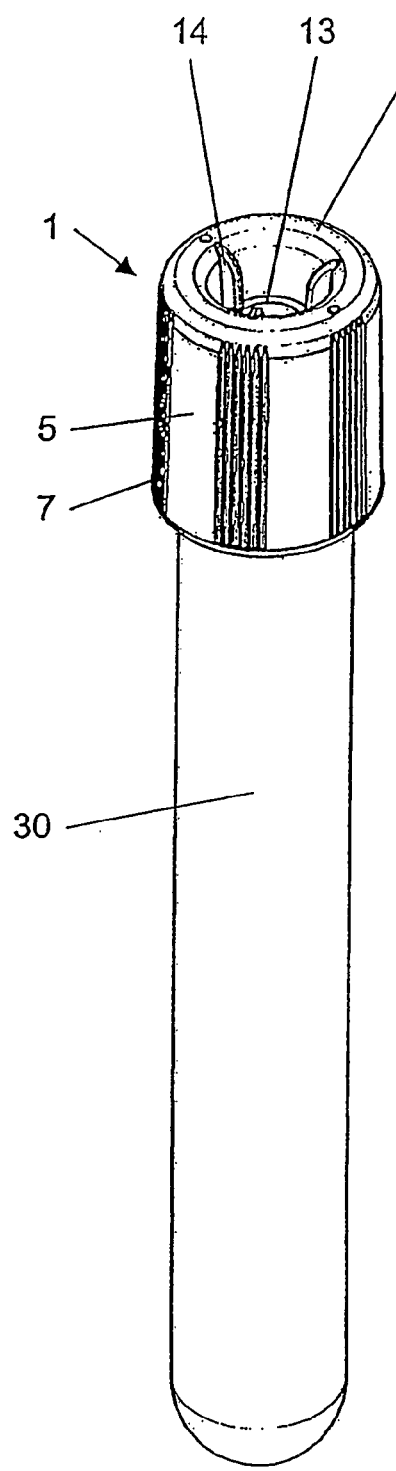
Figure 8:
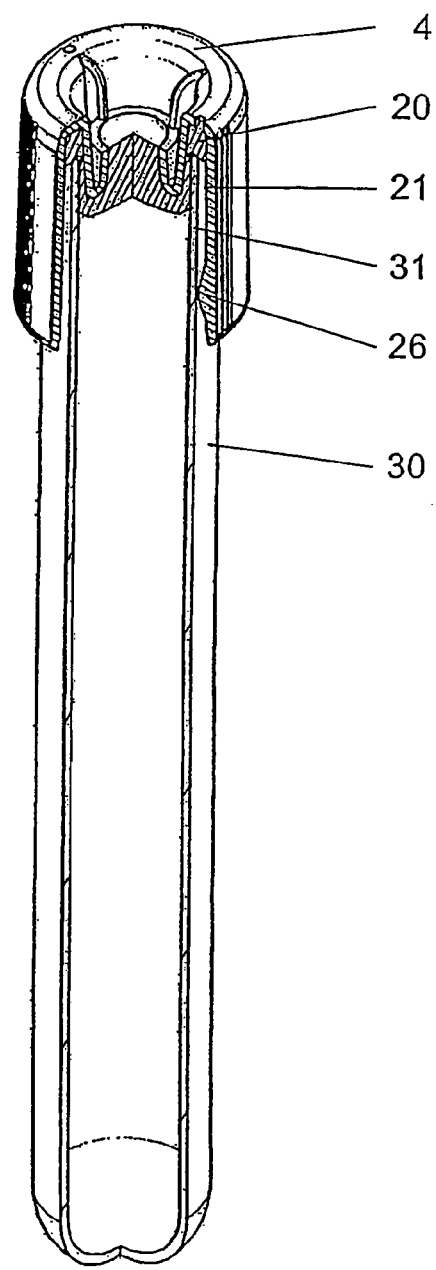
Figure 9:
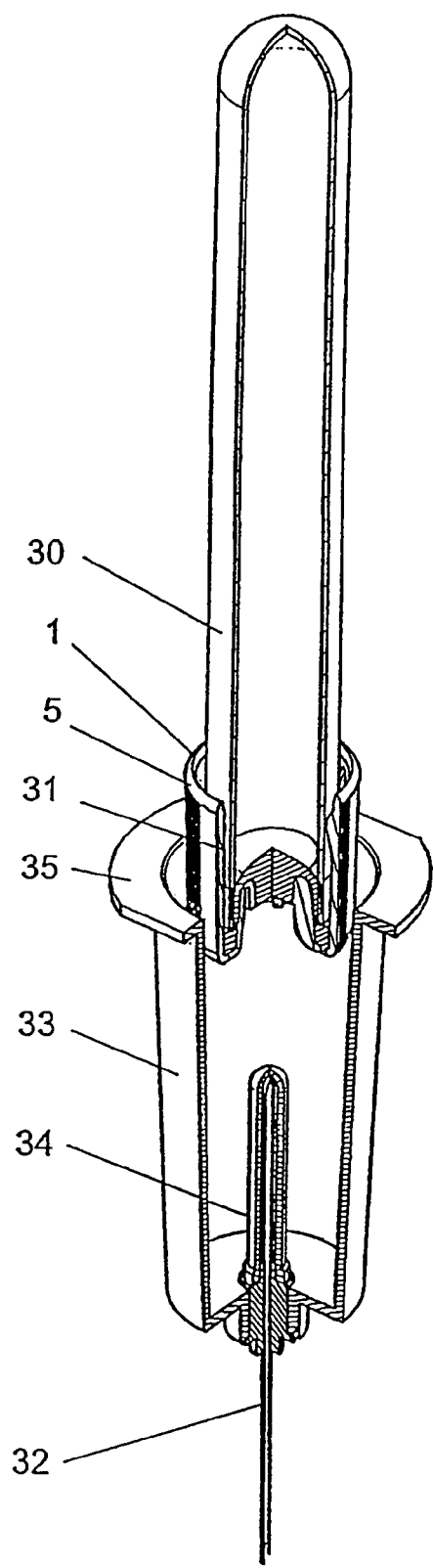
Figure 10:
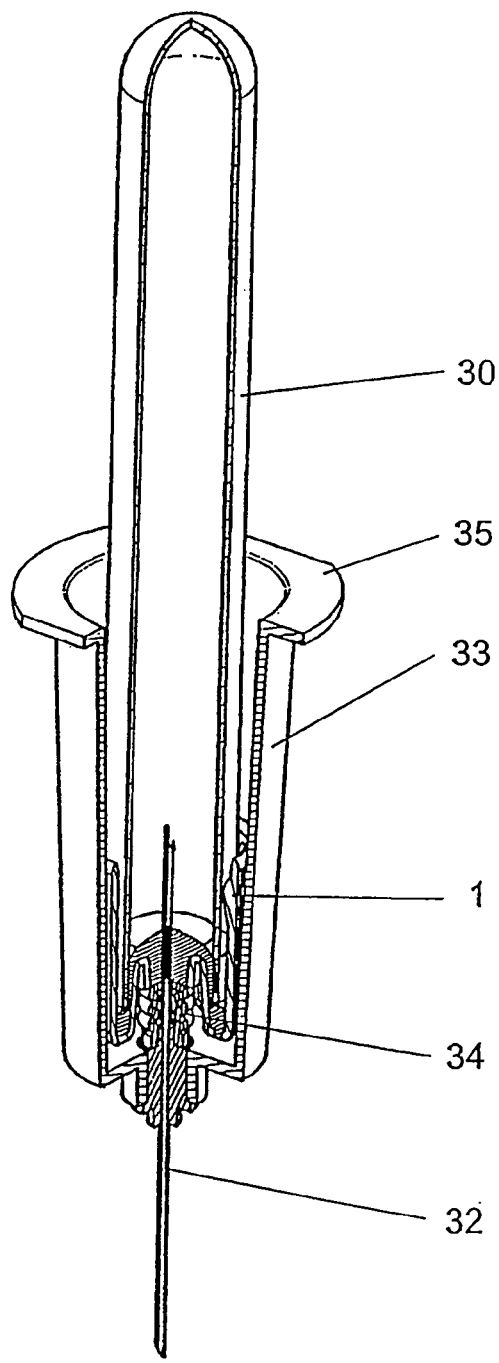

The invention shall be explained in more detail below, with reference to a embodiment depicted in the drawings, wherein FIG. 1 shows a perspective view of the embodiment of a closure device, FIG. 2 shows a further perspective view of said embodiment, with a quarter segment cut away for illustration, FIG. 3 shows a vertical section of an external cap of the closure device, FIG. 4 shows a vertical section of a sealing element of the closure device, FIG. 5 shows a plan view of the closure device, FIG. 6 shows a vertical section of the external cap and the sealing element in their assembled state, FIG. 7 shows a perspective view of a vacuum sample collector in the form of a blood sample tube having a closure device attached thereto, FIG. 8 shows a perspective view of said blood sample tube having said closure device attached thereto, with a quarter segment of said closure device cut away for illustration, FIG. 9 shows the use of said blood sample tube in connection with a double-ended cannula, which is attached approximately centrally on a sleeve-like support, said Figure showing the condition prior to puncture of the closure device, and FIG. 10 shows a perspective view corresponding to FIG. 9, but with the closure device in a punctured state.

The exemplary embodiment depicted in the Figures shows a closure device 1, which shall be explained, in the following, in connection with a vacuum sample collector 30 in the form of a blood sample tube.

FIG. 2 shows the closure device 1 formed by an external cap 2 and a sealing element 3. As shown in FIG. 8, the closure device 1 is placed on a sleeve-like opening portion 31 of a vacuum sample collector 30 in order to seal the latter off against the environment. To this end, the sealing element 3 is arranged on the side of the external cap 2 facing the collector.

The external cap 2 consists of a hard material, preferably plastics, which is referred to hereinafter as a hard-plastic component. However, in principle, it is also possible to manufacture the external cap 2 from metal, if required. In contrast thereto, the sealing element 3 is made of a soft-elastic, preferably gas-impermeable material. Thermoplastics, hereinafter also referred to as soft-plastic component, are particularly suitable to this end.

According to the exemplary embodiment, the external cap 2 is made of polypropylene, while the sealing element 3 consists of rubber.

First of all, the external cap 2 comprises, at an axial end thereof, a front wall 4 surrounded by a side skirt 5. The side skirt 5 is provided as an essentially cylindrical sleeve which, when manufactured by injection molding, is slightly tapered toward said front wall 4, is rearwardly connected to said front wall 4, and is arranged, in the illustrated embodiment, substantially with symmetry of rotation about a central longitudinal axis of the closure device 1. For an improved grip, the outside wall 6 of the side skirt 5 is provided with grooves 7, for example in the form of longitudinal grooves.

The external cap 2 is turned in at its axial or outer front end. The turned-in part 8 extends from the front wall 4, in the form of a depression, into the external cap 2, with the outside wall 9 of the turned-in part 8 tapering slightly conically toward a bottom portion 10 of the depression. The bottom portion 10 is centrally provided with a further, outwardly directed turned-out part, which forms an essentially cylindrical projection 11 at the bottom 10. The projection 11 is provided with a through hole 12, whose opening 13 is arranged within said depression and outside the contact area of a finger in a manner withdrawn from the front end of the external cap 2.

FIG. 2 shows that the through hole 12 is filled completely with material of the soft-plastic component. When taking a blood sample, the soft material located inside the through hole 12 is punctured by a cannula, as shown in FIG. 10. If the blood sample tube 30 comprising the closure device 1 is pulled off the cannula 32 upon taking a blood sample, a drop may be wiped off the cannula, as explained hereinabove, said drop getting caught, first of all, in the depression of the external cap 2, on the outside of projection 11.

A narrow, gap-shaped annular space 15 is formed around the projection 11, into which gap the drop may run. The distance between the outside wall of the projection 11 and the outside wall 9 of the turned-in part 8 is dimensioned to be not more than 1.5 times the wall thickness of the turned-in part 8 on the external cap 2. The annular space 15 should be sufficiently deep to allow an entire drop to be received therein. In the embodiment as shown, the depth of the annular space 15 corresponds to approximately half the distance between the front wall 4 and the bottom portion 10. The gap-shaped design of the space 15 surrounding the projection 11 prevents the drop of blood from spreading over a large area. Instead, such drop is made to collect within said annular space with only a small surface facing the environment. The run-off of such drop may be supported by a slightly outwardly curved design of the front face of said projection 11.

In order to exclude any risk of infection for the person handling the blood sample tube, their fingers should be prevented from touching the projection 11. To this end, the outside wall 9 of the turned-in part 8 is provided with ribs 14, which reduce the free diameter of the depression or of the turned-in part 8, so that not even a fingertip may penetrate as far as the projection 11. The equidistant ribs 14, three in this embodiment, each extend from the front wall 4 to the bottom portion 10. As can be seen, in particular, in FIGS. 2, 3 and 6, the ribs 14 are also connected with the projection 11, so that the annular space 15 is divided, in this case, into three pockets. Each of said pockets on its own is sufficiently dimensioned to receive a drop of usual size. Thus, with the drop running off to one side, a further reduction of the surface area relative to the environment may be achieved. In addition to a reduction of the free diameter, the ribs 14 further had a reinforcing effect on the turned-in part 8 and on the projection 11, thus allowing them to be made thinner than would be possible without said ribs 14.

As is evident, in particular, from FIG. 2, the sealing element 3 tightly fills the smooth-surface through hole 12 of the external cap 2 and terminates at the inside edge 16 of the opening 13, thus forming a thick central sealing plug 17. In addition, the puncture area on the projection 11 is clearly visible. The sealing element 3 further extends along the inside wall 18 of the turned-in part 8 into a circumferential groove 19, which is internally provided at one front end of the external cap 2, between the side skirt 5 and the turned-in part 8. The groove 19 is filled with material of the sealing element 3 which, to this end, comprises a sealing ring portion 20 therein. Between the inside wall 21 of the side skirt 5 and the sealing element 3, there remains an annular gap 22 serving to receive the sleeve-like opening portion 31 of the vacuum sample collector 30 in a sealing manner. Tight sealing is achieved by the sleeve-like opening portion 30 contacting the hard inside wall 21 of the side skirt 5, said opening portion also contacting, however, the sealing ring portion 20 of the sealing element 3 as well as a bridging portion 23 between the sealing ring portion 20 and the sealing plug 17. The elasticity of the sealing element 3 enhances the urging force of the opening portion against the inside wall 21 of the side skirt 5. By contacting the hard-plastic component, the vacuum in the blood sample tube is prevented from being removed by deformation of the sealing element 3 upon inappropriate application of transverse forces to the closure cap 1.

Since the sealing element 3 is not needed to reinforce the external cap 2, the material amount of the soft-plastic component can be kept small.

The closure device 1 shown in the exemplary embodiment is produced by a bicomponent injection molding process, resulting in adhesion between the external cap 2 and the sealing element 3. In order to fill the groove 19, two through holes 24 are provided, according to said embodiment, in the region of the front face 4 of the external cap 2, through which holes the soft component may be injected after manufacture of the external cap 2. The through holes 24 are subsequently also filled with material of the soft component. The corresponding injection-molded projections 25 on the sealing element 3 also provide a smooth external surface in the region of the through holes 24 on the front face 4 of the finished closure device 1. Moreover, this allows the groove 19 to be reliably filled, even if the bridging portion 23 is designed to have very thin walls.

In order to define the closure device 1 on the vacuum sample collector, a portion of the side skirt 5 pulled down over the bottom 10 of the depression on the inside wall 21 of the skirt is provided with engaging projections 26, which cooperate with recesses optionally provided on the sleeve-like opening portion 31 of the container 30. The pulled down portion simultaneously is intended for protection against splashing, when the closure device 1 is removed from the blood sample tube in a laboratory. This will shield any splashing occurring when removing the residual vacuum. Moreover, the bridging portion 23 of the sealing element 3 may be provided with an annular groove 27 to receive a slightly wider edge as sometimes found in blood sample tubes made of glass.

The use of the closure device 1 with a blood sample tube 30 is shown in FIGS. 7 and 8. Thus, when taking a blood sample, first of all, a vein of a person is punctured by one end of a double-ended cannula 32. Alternatively, the cannula 32 may also lead to a further cannula, via a connecting line, to be inserted into a person. To this end, the cannula 32 is centrally attached to one end of a sleeve-like support 33, while the second end of the cannula is enveloped in a foil-like protective coating 34. The support 33 is open at its end opposite the cannula 32, where it additionally comprises an essentially radially extending holding collar 35. The blood sample tube 30 comprising the closure device 1 is inserted through the open end and urged against the second end of the cannula 32. Both the foil-like protective coating 34 and the through hole 12 or the sealing plug 17 of the closure device 1 are centrally punctured. Then, the blood sample tube 30 is filled, utilizing the vacuum prevailing in the blood sample tube 30.

Upon said filling, the blood sample tube 30 is pulled off the cannula 32 and taken to a laboratory. If required, further similar blood sample tubes 30 are filled in the above-described manner, until the cannula 32 is pulled out of the vein upon filling the last tube. The sealing plug 17 automatically closes the opening created by the cannula 32, so that contamination of the sample with foreign substances from the environment is avoided. The above-described embodiment of the closure device 1 guarantees non-infectious transport of the sample to the laboratory.

The invention claimed is:

1. A closure device for a vacuum sample collector, comprising an external cap (2) made of a hard material, preferably a hard-plastic component, with a front wall (4) and a side skirt (5) and at least one through hole (24) leading to a groove (19) which surrounds said front wall and may be attached to a sleeve-like opening portion (31) of the vacuum sample collector (30), and a sealing element (3) arranged on the container side of the external cap (2) and made of an elastic sealing material, preferably a soft plastic component which extends up to an inside edge (16) of opening (13) having a planar top surface terminating at the inner edge of said opening (13), the external cap (2) being made of a gas-impermeable material and the sealing element (3) being made of an elastomer, the front wall (4) of the external cap (2) being turned in to form a depression, and the bottom (10) of said turned-in part (8) in turn being turned-out, and said turned-out part being provided as an essentially hollow, cylindrical projection (11) comprising a smooth surface through hole (12), whose opening (13) is distanced from a front end of the external cap (2) and is disposed axially below through hole 24 to be outside a contact area of a finger, and that a narrow, gap-shaped annular space (15) not more than 1.5 times the wall thickness of the turned in part (8) is formed between the outside wall of the cylindrical projection (11) and the inside wall (9) of the inwardly directed, turned-in part (8), wherein the sealing element (3) fills the through hole (12) and further lines the inside wall (18) of the turned-in part (8) as well as a groove (19), which is formed on the inner side of the front end of the external cap (2) between the side skirt (5) and the turned-in part (5), whereby a gap (22) is formed on the inside wall (21) of the side skirt (5) to receive, in a sealing manner, the sleeve-like opening portion (31) of the vacuum sample collector (30), characterized in that the radial circumferentially spaced ribs (14) on the inside wall (9) of the inwardly directed, turned-in part (8) extend into the annular channel (16) from the front wall (4) to the bottom portion (10), the circumferentially spaced ribs (14) dividing the channel into a plurality of pockets extending from the front wall (4) to the bottom (10) to thereby reduce the free diameter of the turned-in part.

2. The closure device as claimed in claim 1 characterized in that the external cap (2) is made of gas-impermeable material, preferably polypropylene, and the sealing element (3) is made of an elastomer, preferably rubber.

3. A vacuum sample collector, preferably for use in taking blood samples, said collector comprising a container (30) having a sleeve-like opening portion (31) which is sealed by a closure device (1) as claimed in claim 1 with a vacuum prevailing in said container (30).

* * * * *